United States Patent
Lazarus et al.

(10) Patent No.: US 7,087,573 B1
(45) Date of Patent: Aug. 8, 2006

(54) METHODS OF INHIBITING PLATELET ANTI-HLA ALLOIMMUNE ANTIBODY RESPONSES WITH SOLUBLE 18 KDA CD40L

(75) Inventors: Alan H. Lazarus, Toronto (CA); Andrew R. Crow, East York (CA); John Freedman, Toronto (CA)

(73) Assignee: Canadian Blood Services (CA)

( * ) Notice: Subject to any disclaimer, the term of this patent is extended or adjusted under 35 U.S.C. 154(b) by 0 days.

(21) Appl. No.: 09/579,548

(22) Filed: May 26, 2000

Related U.S. Application Data

(63) Continuation of application No. PCT/CA98/01105, filed on Nov. 27, 1998.

(30) Foreign Application Priority Data

Nov. 28, 1997 (CA) .................................. 2223225

(51) Int. Cl.
*A61K 38/16* (2006.01)
*A61K 38/19* (2006.01)

(52) U.S. Cl. .............. 514/8; 514/2; 514/885; 424/85.1; 424/278.1; 530/350; 530/351

(58) Field of Classification Search ............. 424/133.1, 424/85.1, 184.1; 514/2, 8, 885; 530/350, 530/351, 387.3
See application file for complete search history.

(56) References Cited

U.S. PATENT DOCUMENTS

| 5,540,926 | A | 7/1996 | Aruffo |
| 6,264,951 | B1 * | 7/2001 | Armitage et al. |
| 6,376,459 | B1 * | 4/2002 | Aruffo et al. |
| 6,440,418 | B1 * | 8/2002 | Black et al. |
| 2001/0026932 | A1 * | 10/2001 | Thomas et al. .......... 435/70.21 |

OTHER PUBLICATIONS

Harrington et al. Vox Sang. 51 (suppl L):18-21 (1986).*
Lazaraus Transfusion 39:818-823 (1999).*
Nannizzi-Alaimo et al. Circulation 105:2849-2854 (2002).*
Semple et al. Blood 100: 1055-1059 (2002).*
Bankert et al. Trends in Immunology 22:386-393 (2001.*
Krishna et al. Arthritis & Rheumatism 42: 871-881, 1999.*
Ludewig et al. Eur. J. Immunol. 26: 3137-3143, 1996.*

* cited by examiner

*Primary Examiner*—Phillip Gambel
(74) *Attorney, Agent, or Firm*—Nixon Peabody LLP

(57) ABSTRACT

The invention relates to a method for inhibiting an in vivo alloimmune response, and to the use of a soluble recombinant human CD40L protein containing the active binding site with CD40. In particular, a soluble 18 KDa recombinant CD40L is used to inhibit an in vivo alloimmune response.

1 Claim, 6 Drawing Sheets

SEQUENCE LISTING

```
<160> NUMBER OF SEQ ID NOS: 1

<210> SEQ ID NO 1
<211> LENGTH: 261
<212> TYPE: PRT
<213> ORGANISM: unknown
<220> FEATURE:
<223> OTHER INFORMATION: human CD40L protein or fragment thereof

<400> SEQUENCE: 1
```

Met Ile Glu Thr Tyr Asn Gln Thr Ser Pro Arg Ser Ala Ala Thr Gly
 1               5                  10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

-continued

```
Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

METHODS OF INHIBITING PLATELET ANTI-HLA ALLOIMMUNE ANTIBODY RESPONSES WITH SOLUBLE 18 KDA CD40L

This application is continuation application of International Application No. PCT/CA98/01105, filed, Nov. 28, 1998.

BACKGROUND OF THE INVENTION (a) Field of the Invention

The invention relates to a method for inhibiting in vivo immune response and to the use of a soluble recombinant human CD40L or a sequence within said soluble recombinant human CD40L containing the active binding site with CD40 for inhibiting an immune response. The invention also relates to a mouse model of human alloimmunization for testing in vivo effects of an immunotherapy or inhibition of a human antibody response.

(b) Description of Prior Art

Platelet alloimmunization occurs as a result of exposure to "foreign" antigens present in pooled random donor platelet concentrates. A consequence of platelet alloimmunization is the development of a state of refractoriness to subsequent random donor platelet transfusion. Up to 50% of patients with acute leukemia, almost 100% of those with aplastic anemia and 10% of patients with solid tumors, develop platelet alloantibodies. The alloantibodies are most often directed against HLA Class I antigens, although in 10–20% of cases they are directed against platelet-specific antigens such as $Pl^{A}$, Bak, Pen. Effective platelet support for such patients is dependent upon provision of compatible platelets selected by HLA matching and/or platelet crossmatching, approaches which are expensive and, in up to one-third of cases, ineffective. A multitude of clinical and experimental studies have indicated that alloimmunization depends upon (or is at least augmented by) the presence of "contaminating" MHC class II bearing antigen presenting cells (APC) in the transfused blood products.

Investigators have attempted to inactivate donor APC by ultraviolet radiation, or have applied leukofiltration to remove the APC from the transfused product. Most studies, including a large US-based multi-centre study (TRAP, Trial to Reduce Alloimmunization to Platelets) have indicated that the frequency of patients that become alloimmunized is decreased when leukofiltered products are used. However, it is important to note that although these studies reduced the incidence of alloimmunization by approximately 50%, many patients still become alloimmunized.

The major co-stimulatory molecule for B cells is the CD40 molecule. This surface membrane protein which is found on B cells as well as some other cells interacts with a molecule on activated Th cells designated as CD40 ligand (CD40L, gp39 or CD154) CD40-CD40L interaction is critical to B cell activation and differentiation. B cells stimulated with anti-CD40 antibodies undergo transmembrane signaling, cell enlargement, and LFA-1-dependent aggregation. When B cells are stimulated via an appropriate stimuli in combination with anti-CD40, these B cells can proliferate or be induced to isotype switch depending upon the first stimulus. Patients with defective CD40L function have X-linked hyper-IgM syndrome characterized in part by low levels of serum IgG, IgA, and IgE. CD40 and CD40L deficient mice have numerous immune defects including the inability to class switch from IgM to $IgG_1$ and the inability to stimulate allogenic T cells in an in vitro mixed lymphocyte reaction (MLR). Injection of animals with anti-CD40L antibody has been shown to inhibit both a primary and secondary antibody response, as well as prevent the occurrence of anti-DNA antibodies and disease pathology in lupus-prone mice. Further, administration of a soluble form of CD40L to human B cell hybridomas can induce apoptosis (U.S. Pat. No. 5,540,926). While the CD40 molecule on the B cell provides co-stimulation to that cell via interaction with a Th cell expressing the CD40L, it is important to note that the T cell also becomes activated by this mutually synergistic interaction.

It would be highly desirable to be provided with a method to inhibit in vivo alloimmunization.

SUMMARY OF THE INVENTION

One aim of the present invention is to provide a method for inhibiting human anti-HLA alloimmune response.

In accordance with the present invention there is provided a use of a soluble recombinant human CD40L or a functional fragment thereof containing the active binding site of CD40 and capable of binding thereto, for inhibiting an immune response. Preferably, the soluble recombinant human CD40L has a sequence comprised in amino acids 108 to 261 of the following sequence:

```
Met Ile Glu Thr Tyr Asn Gln Thr Ser Pro Arg Ser Ala Ala Thr Gly       SEQ ID NO:1
 1           5                  10                 15

Leu Pro Ile Ser Met Lys Ile Phe Met Tyr Leu Leu Thr Val Phe Leu
            20                  25                 30

Ile Thr Gln Met Ile Gly Ser Ala Leu Phe Ala Val Tyr Leu His Arg
            35                  40                 45

Arg Leu Asp Lys Ile Glu Asp Glu Arg Asn Leu His Glu Asp Phe Val
       50                  55                 60

Phe Met Lys Thr Ile Gln Arg Cys Asn Thr Gly Glu Arg Ser Leu Ser
65                  70                 75                 80

Leu Leu Asn Cys Glu Glu Ile Lys Ser Gln Phe Glu Gly Phe Val Lys
                85                  90                 95

Asp Ile Met Leu Asn Lys Glu Glu Thr Lys Lys Glu Asn Ser Phe Glu
                100                 105                110
```

-continued

```
Met Gln Lys Gly Asp Gln Asn Pro Gln Ile Ala Ala His Val Ile Ser
    115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
                260
```

The immune response inhibited is preferably an alloimmune response, and more preferably a human anti-HLA alloimmune response.

In accordance with the present invention, there is also provided a soluble recombinant human CD40L or a functional fragment thereof containing the active binding site of CD40 and capable of binding thereto, as described above, for inhibiting T cell function. Preferably, the soluble recombinant human CD40L or the functional fragment thereof can be used for treating or preventing T cell dependent or T cell mediated diseases selected from the group consisting of autoimmune diseases, including systemic lupus erythematosus (SLE), sjögren's syndrome, sleroderma myositis, Raynaud's syndrome, type 1 diabetes, arthritis and rheumatoid arthritis, inflammatory bowel disease, uveitis, myesthenia gravis, multiple sclerosis, idiopathic thrombocytopenic purpura and graft vs host disease as well as allergies which are dependent on T cells.

In accordance with the present invention, there is also provided the use of a soluble recombinant human CD40L or a functional fragment thereof containing the active binding site of CD40 and capable of binding thereto, for the preparation of a medicament for immunotherapy or for treating or preventing a disease selected from the group consisting of SLE, type 1 diabetes, multiple sclerosis, idiopathic thrombocytopenic purpura and graft vs host disease.

Further in accordance with the present invention, there is provided an immunodeficient mouse model of human alloimmunization for testing in vivo effects of an immunotherapy or inhibition of a human antibody response, characterized in that the mouse model is a severe combined immunodeficient (SCID) mouse, reconstituted with human peripheral blood lymphocytes (PBL) from donors. Preferably, the donors are sensitized to HLA antigens.

Preferably, the SCID mouse is γ-irradiated and asialoGM₁ treated for enhancing cellular engraftment.

Also in accordance with the present invention, there is provided a method for inhibiting an immune response in a patient, comprising the step of administering a therapeutically effective amount of a soluble recombinant human CD40L or a functional fragment thereof containing the active binding site of CD40 and capable of binding thereto.

In accordance with the present invention, there is also provided a method for inhibiting T cell function in a patient, comprising the step of administering a therapeutically effective amount of a soluble recombinant human CD40L or a functional fragment thereof containing the active binding site of CD40 and capable of binding thereto.

Preferably, the method for inhibiting T cell function is used for treating or preventing T cell dependent or T cell mediated diseases selected from the group consisting of autoimmune diseases, including systemic lupus erythematosus (SLE), sjögren's syndrome, sleroderma myositis, Raynaud's syndrome, type 1 diabetes, arthritis and rheumatoid arthritis, inflammatory bowel disease, uveitis, myesthenia gravis, multiple sclerosis, idiopathic thrombocytopenic purpura and graft vs host disease as well as allergies which are dependent on T cells.

DETAILED DESCRIPTION OF THE INVENTION

Figure 1A:
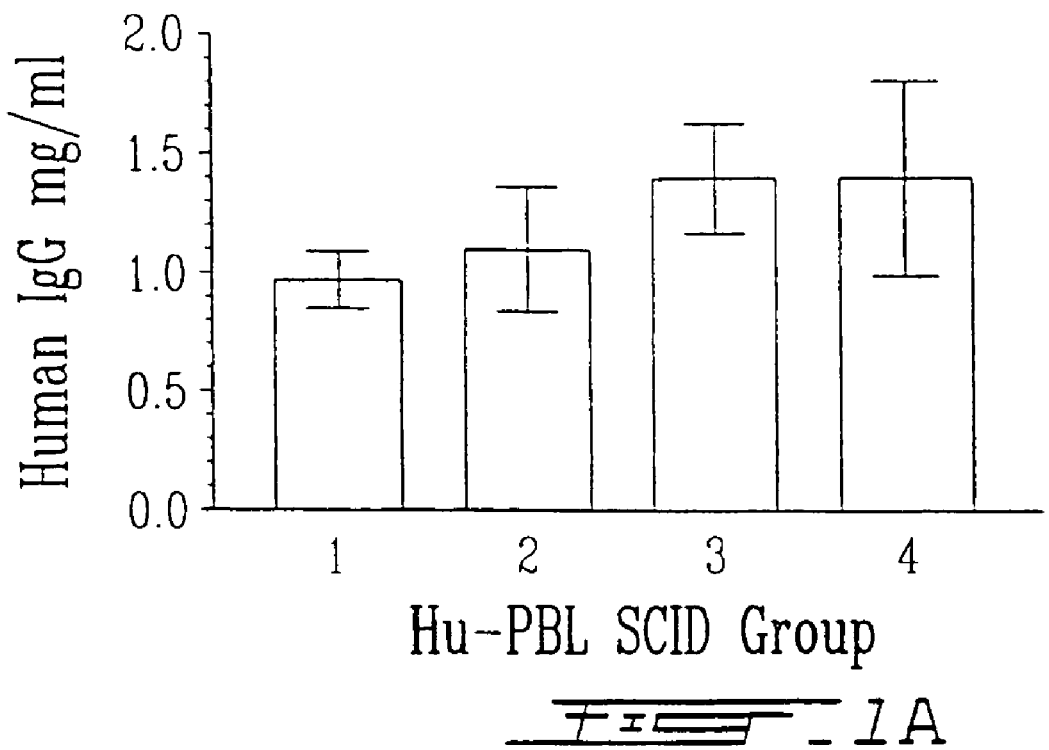
FIG. 1A represents an histogram illustrating the measurements of the total IgG from Hu-PBL-SCID mice on day 18 post-engraftment by ELISA.

The method of the present invention has been evaluated using a Hu-PBL-SCID mouse model. This immunodeficient mouse model, developed for the present invention, is a valuable model for testing in vivo effects of novel immunotherapies or inhibition of the human antibody response.

In accordance with the method of the present invention, it is proposed that anergy induction via inhibition or inappropriate activation of the CD40-CD40L co-stimulatory cascade, is effective in inhibiting an in vivo immune response. It is believed that the soluble recombinant CD40L active fragment competes B cell- (or APC-) CD40 interaction with CD40L on the TH cell which disallows the TH cell to be activated to secrete cytokines (such as Th2 cytokines) which thus reduce the transfusion-induced alloimmune response.

To develop an in vivo experimental model of human alloimmunization that would be amenable to experimental manipulation, a model was developed, in which mice with severe combined immunodeficiency (SCID) are repopulated with human peripheral blood lymphocytes (Hu-PBL-SCID) from healthy blood donors and challenged with HLA-mismatched lymphocytes.

An in vivo model of human alloimmunization was evaluated using severe combined immunodeficient (SCID) mice. SCID mice were irradiated (200 cGy), and reconstituted with human peripheral blood lymphocytes (PBL) from donors sensitized to HLA antigens by prior pregnancy. The reconstituted SCID mice (Hu-PBL-SCID) were then challenged with HLA-mismatched PBL. Alloantibodies were evaluated by flow cytometry (42) and a standard two stage microlymphocytotoxicity (LCT) assay (40).

The Hu-PBL-SCID mice (N=22) that were challenged with PBL expressing the HLA antigens to which the donors had previously been sensitized, made significantly increased levels of both IgM and IgG alloantibodies as compared to unchallenged mice. Responses were measurable by 1 week post reconstitution and challenge. Prior treatment of SCID mice with anti-asialo-$GM_1$, which depletes murine NK cells and macrophages, further increased the alloantibody response of challenged mice. The human alloantibodies generated were specific for the challenge HLA antigens as assessed by LCT.

Hu-PBL-SCID mice were divided into 4 groups.

Group 1 consists of mice reconstituted with PBL from donor A (as described herein except that $10^7$ PBL were used to reconstitute the mice). These animals were bled twice weekly (18 KDa CD40L-untreated and HLA-unchallenged negative control group).

Group 2 consists of mice similar to the ones of Group 1, except that the mice were injected with 200 μg of 18 KDa CD40L via the intraperitoneal route on the day of reconstitution (18 KDa CD40L-treated and HLA-unchallenged negative control group).

Group 3 consists of mice similar to the ones of Group 1, except that the mice also received twice weekly challenges with HLA-mismatched lymphocytes (18 KDa CD40L-untreated and HLA-challenged positive control group).

Group 4 consists of mice similar to the ones of Group 1, except that the mice were injected with 200 μg of 18 KDa CD40L via the intraperitoneal route on the day of reconstitution and also received twice weekly challenges with HLA-mismatched lymphocytes (18 KDa CD40L-treated and HLA-challenged experimental group).

Figure 1B:
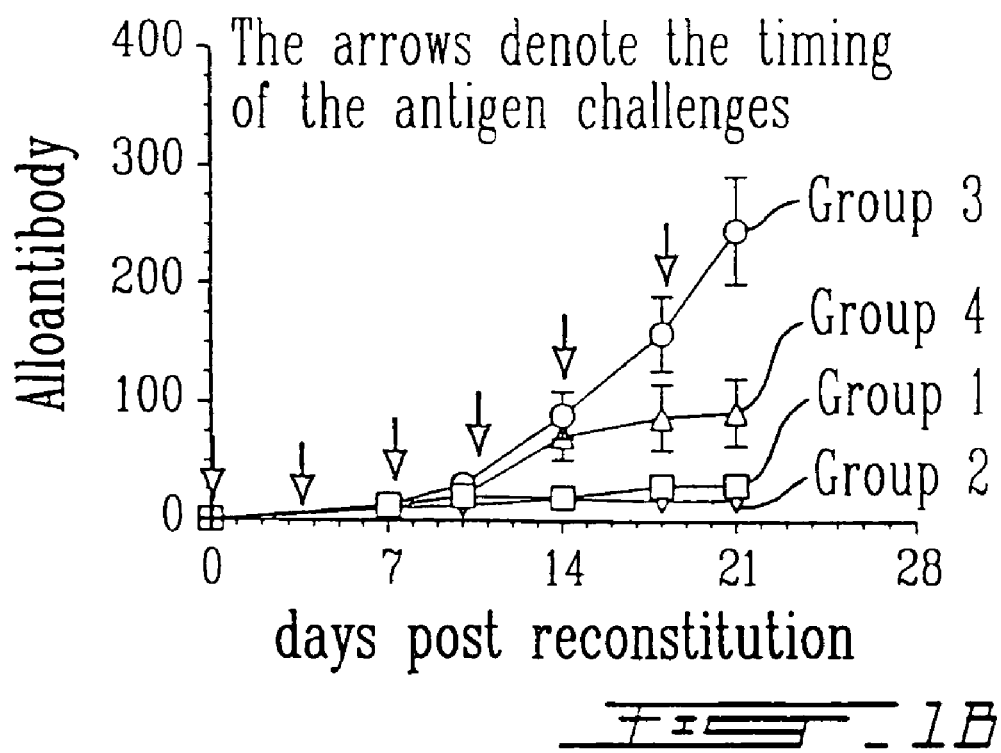
FIG. 1B represents a plot chart illustrating the measurements of human alloantibody from Hu-PBL-SCID mice by flow cytometry.

All mice were examined for total human IgG levels as a measure of the success of functional cellular engraftment as well as to determine if the recombinant soluble 18 KDa CD40L protein product inhibits or affects B cell IgG production. FIG. 1A shows that the total level of human IgG as measured after 18 days of human PBL engraftment is not statistically different in any of the groups. For the purposes of this disclosure, this indicates that the soluble CD40L therapeutic does not adversely affect either cellular engraftment nor does it inhibit the ability of human B cells to produce immunoglobulin. It is therefore unlikely that the CD40L therapeutic induces B cell apoptosis or non-specific B cell anergy when administered in vivo. The numbers under each bar indicate the group number corresponding to those of FIG. 1B. Next, in FIG. 1B, the ability of each group of mice to make alloantibody was examined. Groups 1 and 2 did not make significant levels of alloantibody (i.e. no anti-HLA antibody), as expected. Group 3 made enhanced levels of alloantibody, as expected. Group 4 which received a single dose of the soluble 18 KDa CD40L therapeutic made significantly less alloantibody than did group 3.

Administration of a single 200 μg inoculation of soluble recombinant 18 KDa, CD40L active component was able to significantly decrease the human alloimmune antibody response to challenge with HLA-mismatched blood cells in a humanized SCID model system. This work therefore shows that in vivo administration of a single dose of soluble recombinant CD40L active component can inhibit a specific antibody response. Moreover, T cell proliferation was also prevented in vitro in a mixed lymphocyte culture. Therefore, T cell function was also inhibited by the soluble recombinant 18 KDa CD40L active component.

Preparation of a Hu-PBL-SCID Mouse Model

SCID Mice

C.B.17 SCID virgin female mice (6–8 weeks of age) were obtained from the Hospital for Sick Children, Toronto, Ontario and were housed under gnotobiotic conditions in the St. Michael's Hospital research vivarium. Blood from the tail vein (300 μl) was collected into untreated microvette tubes (Sarstedt, Montreal, Quebec) and the serum was separated after incubation for 2 h at 22° C. Serum levels of endogenous murine IgG were determined by ELISA and animals with a serum murine immunoglobulin concentration exceeding 10 μg/ml ("leaky" phenotype) were excluded from the study. Commencing 1 week post reconstitution, mice were bled twice weekly for 5 weeks, and weekly thereafter until day 70 post reconstitution.

Reconstituting PBL Donors

Female blood donors with a history of prior pregnancy were screened for evidence of circulating HLA class I alloantibodies. With informed consent, blood samples were obtained at the time of whole blood or platelet apheresis donations and were tested using a standard NIH microlymphocytotoxicity test against a panel of 30 HLA-typed lymphocytes (40). Donor "A" was blood group O, HLA A1, A3, B7 and B37 positive and had low levels of circulating anti-HLA-A2 and anti-HLA-B5 alloantibodies. Donor "B" was group A, HLA A1, A2, B7 and B8 positive and had low levels of circulating anti-HLA-A10 and anti-B5, -B12 and -B17 alloantibodies.

PBLs from the donor used to reconstitute the Hu-PBL-SCID mice were cultured in vitro ($2\times10^5$/well) with the same γ-irradiated cells used to challenge the mice ($4\times10^5$/well), with or without 18 KDa-CD154 for 72 h in a final volume of 200 ml in RPMI-1640 containing 10% fetal calf serum (FCS), 100 U/ml penicillin G, 100 mg/ml streptomycin sulfate, 0.25 mg/ml Amphotericin B as fungizone (Gibco-BRL, Grand Island, N.Y.), 100 mM L-glutamine, and $5\times10^{-5}$ M 2-mercaptoethanol (CRPMI), in 96-well flat bottomed tissue culture grade plates at 37° C. Plates were then pulsed with 1 mCi $^3$H-thymidine for 24 h, wells were harvested onto filter paper and incorporated radioactivity assessed by scintillation counting. For in vitro IgG production, plates were cultured with cells as above and were maintained for 18 days by replenishing CRPMI every 3 days. The plates were centrifuged at 300×g for 5 min on day 18 and the supernatant fluid assessed for human IgG levels by ELISA.

Reconstitution

All SCID mice were exposed to 200 cGy of irradiation prior to reconstitution to enhance cellular engraftment. To deplete NK cells, some SCID mice were injected with 20 µl of anti-asialoGM$_1$ antisera (Wako Pure Chemical Industries LTD, Dallas, TX) 1 day prior to reconstitution. One unit of whole blood was collected into standard collection bags containing CP2D (Citrate Phosphate Double Dextrose); following centrifugation at 4550×g for 3.2 min and removal of the supernatant plasma, buffy coats were transferred into a satellite bag. To obtain human PBL, the buffy coat was layered onto a 1.077 g/L Percoll™ (Pharmacia LKB, Baie d'Urfe, Quebec) gradient and separated by centrifugation (1200×g for 30 min at 22° C.). The PBL were washed three times with phosphate-buffered saline, pH 7.4 (PBS), adjusted to a concentration of $8\times10^7$/ml in 80% FCS in RPMI-1640, and 0.5 ml injected into the peritoneal cavity of recipient SCID mice using a 27 gauge needle.

SCID Mice Challenge

Challenge leukocytes were obtained from heparinized blood and isolated by Percoll density centrifugation as described above. Mice reconstituted with donor "A" cells were challenged with human PBL from HLA-A2 antigen positive blood donors and those reconstituted with donor "B" cells were challenged with human PBL from HLA-A10 antigen positive blood donors. A large number of different donors were used for each challenge; all expressed the pertinent challenge antigen, but expressed a variety of other antigens as well. In a separate experiment, Hu-PBL-SCID mice reconstituted with cells from donor "A" were challenged with cells from 4 individuals expressing only HLA A2, and B5 as antigens foreign to donor "A".

All challenge cells were γ-irradiated with 2500 cGy prior to administration to prevent engraftment in recipient mice. The first challenge consisted of $2\times10^7$ PBL/mouse and subsequent immunizations were with $10^7$ PBL/mouse. Immunizations with pooled γ-irradiated PBL (in 0.5 ml of 80% fetal calf serum in RPMI-1640) were performed twice weekly for 3 weeks starting on the day of reconstitution.

Detection of Mouse or Human Immunoglobulin

ELISA plates were coated with of 1.25 µg/ml of either goat antimouse or antihuman IgG+IgM (50 µl/well; Caltag-Cedarlane Laboratories, Hornby, Ont.) in 50 mM carbonate/bicarbonate buffer, pH 9.6, for 18 h at 4° C. The plates were then washed three times with washing buffer (0.05% Tween 20/PBS), blocked with 0.2% Tween 20/PBS (200 µl/well) for 2 h at 37° C., and again washed three times with washing buffer. Sera from the mice were serially diluted in PBS, added to the plates (25 µL/well), and incubated for 2 h at 22° C. Serially diluted normal mouse or human serum and purified mouse or human IgG were used as controls and standards. The plates were washed three times in washing buffer and 25 µl of alkaline phosphatase-conjugated F(ab')$_2$ goat antimouse or antihuman IgG or IgM (Cedarlane Laboratories) was added. After incubation at 22° C. for 2 h, the plates were washed four times and 100 µl of substrate solution (5 mM p-Nitrophenyl phosphate; BioRad Laboratories, Mississauga, Ontario) was added and absorbance was measured at 405 nm. The concentration of IgG and IgM was calculated based upon a standard curve.

Alloantibody Detection

Alloantibodies were detected by flow cytometry as previously described (42) or by a microlymphocytotoxicity test (LCT) (40) using HLA typed target cells. For flow cytometric analysis, SCID sera were diluted 1:10 and incubated with $2\times10^5$ fresh HLA typed antigen positive lymphocytes in a volume of 20 µl for 1 h at 22° C. The cells were then washed twice and incubated at 22° C. for 1 h in 100 µl each, of 1 µg/ml of affinity-purified fluorescein isothiocyanate (FITC)-labeled F(ab')$_2$ antihuman IgG, Fc-specific antibody and 0.5 µg/ml of affinity-purified phycoerythrin (PE)-labeled F(ab')$_2$ antihuman IgM, µ specific antibody (Tago; Biosource, Camarillo, Calif.). The cells were then washed twice and fixed in 1% paraformaldehyde in PBS. Cells were analyzed by flow cytometry as described previously (42). Background staining was assessed by comparison with a serum obtained from each animal prior to any manipulation. Antibody specificity for HLA antigens was confirmed using neat sera in the standard two-stage complement-dependent microlymphocytotoxicity assay using a typed panel of lymphocytes from donors (40); a positive result was defined as >20% lysis of target cells, unless otherwise stated.

IgG Depletion

Sera from NK-depleted challenged Hu-PBL-SCID mice were pooled and depleted of IgG by affinity chromatography. A saturating quantity of purified goat anti-human IgG, Fc-specific antibody (Atlantic Antibodies, Scarborough Me.) was coupled to CNBr-activated sepharose™ 4B media according to the manufacturers directions (Pharmacia Biotech, Baie d'Urfé, PQ). The beads were blocked with excess glycine and extensively washed. Fifty (50) µl of mouse sera was added to 100 µl of packed anti-IgG coated beads with constant mixing for 1 hour at 25° C. followed by removal of the supernatant fluid. This IgG-depletion was verified to reduce the IgG content of the pooled sera from 3.2 mg/ml IgG to 20 µg/ml by ELISA. This IgG-depleted sera (referred to as "pooled IgM" in Table 1 below) was then added to another 100 µl of packed fresh anti-IgG coated beads with constant mixing for 1 hour and used in the LCT.

Figure 2A:
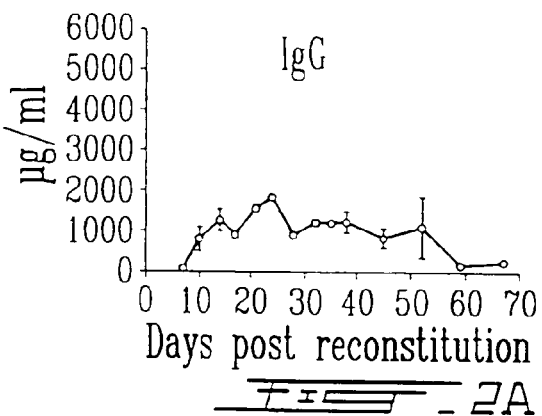
FIGS. 2A to 2F illustrate mean±SEM concentrations of human IgG and IgM in SCID mice reconstituted with PBL from a donor.
Figure 2B:
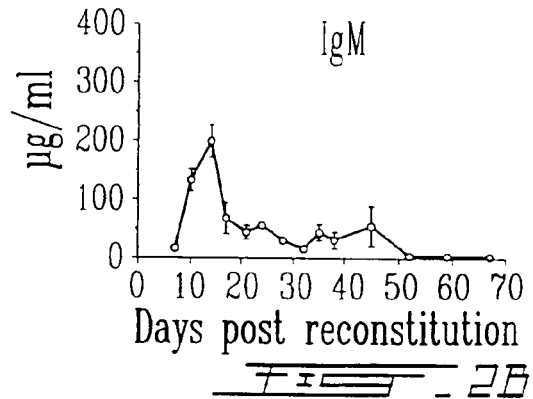
Figure 2C:
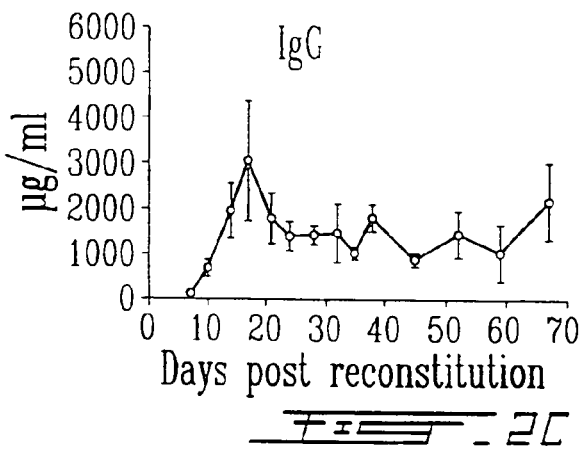
Figure 2D:
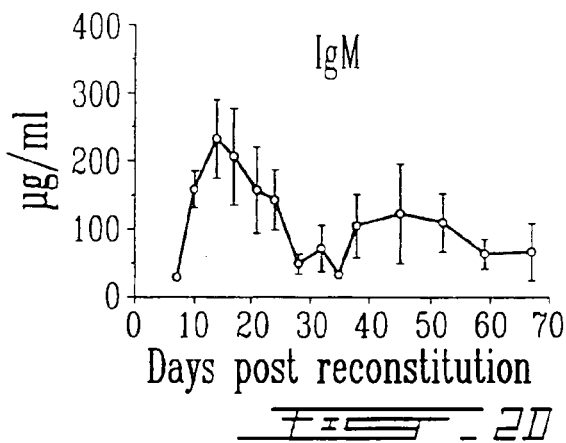

Ten (10) SCID mice were reconstituted by ip injection with $4\times10^7$ PBL and were either not further manipulated or received twice weekly ip challenge with HLA-mismatched γ-irradiated lymphocytes for 3 weeks commencing on the day of reconstitution. Challenge lymphocytes were derived from between 8–12 different donors for each challenge. These mice are hereafter referred to as "challenged mice". Both challenged and unchallenged mice made human IgG and IgM immunoglobulin (FIGS. 2A and 2B), indicating that the mice were successfully engrafted with human cells. Human IgG levels in unchallenged and in challenged mice reached plateau levels by 14 days post reconstitution and showed little variation until approximately 50 days post-reconstitution (FIGS. 2A and 2C). Human IgM levels in unchallenged and challenged mice were similar until day 32 post-reconstitution (FIGS. 2B and 2D).

Figure 2E:
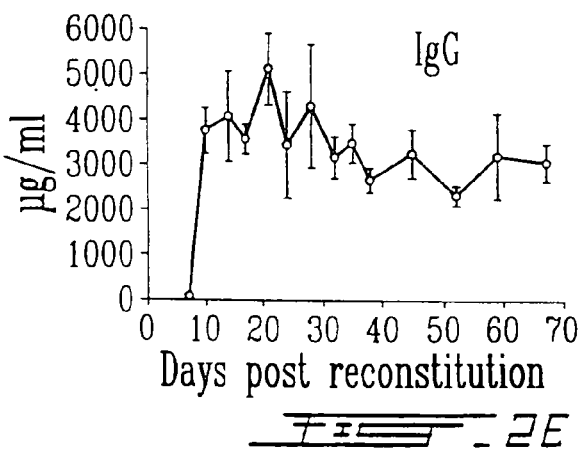
Figure 2F:
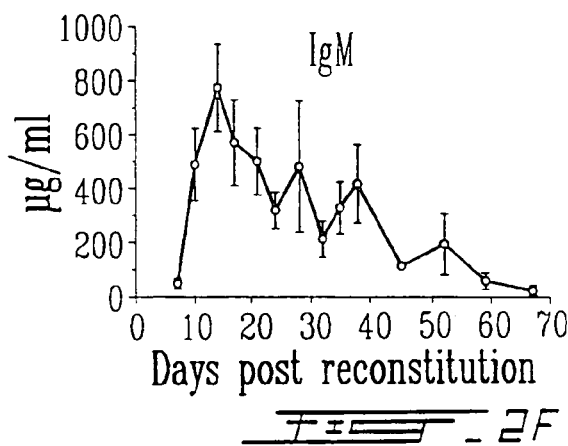

Total serum human IgG (FIGS. 2A, 2C and 2E) and IgM (FIGS. 2B, 2D and 2F) were quantitated by ELISA. SCID mice were either reconstituted and not challenged (FIGS. 2A and 2B, n=4 mice), reconstituted and challenged with HLA-A2 antigen positive lymphocytes (FIGS. 2C and 2D, n=7 mice) or pretreated with anti-asialoGM$_1$, reconstituted and challenged with HLA-A2 antigen positive lymphocytes (FIGS. 2E and 2F, n=14 mice).

SCID mice reconstituted with lymphocytes from donor "A" who had anti-HLA-A2 and -B5 alloantibody were either left unchallenged or challenged with HLA-A2 antigen positive cells. Sera from these mice were tested for allo-reactive IgG and IgM antibody by flow cytometry at each bleed.

Figure 3A:
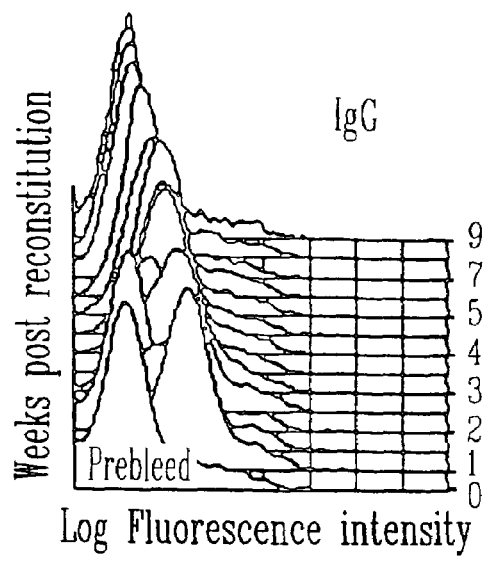
FIGS. 3A to 3F illustrate flow cytometric analysis of alloantibody production in representative SCID mice reconstituted with PBL from a donor "A" who was previously sensitized to HLA-A2.
Figure 3B:
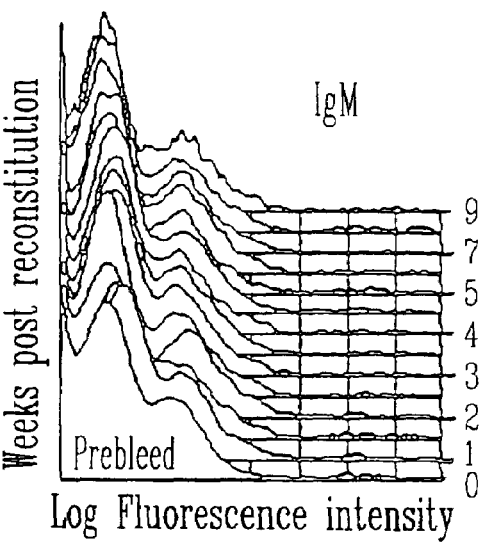
Figure 3C:
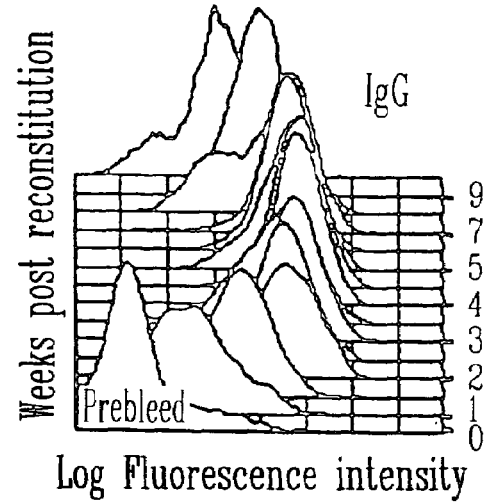
Figure 3D:
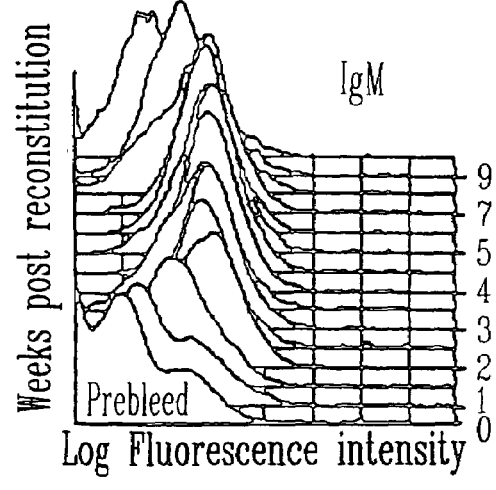

FIGS. 3A to 3F show reactivity of sera from a typical mouse from each experimental group against HLA-A2 target lymphocytes. The histograms represent consecutive bleeds over the time period shown by the number of weeks post reconstitution on the right Y-axis. Shorter periods shown indicate that the mice died prior to the next bleed date. Hu-PBL-SCID mice that remained unchallenged made a low level of IgG allo-reactive antibody measurable by day 7 post-reconstitution that did not further increase with time over the study period (FIG. 3A). The unchallenged Hu-PBL-SCID mice did not have allo-reactive IgM antibody detectable by flow cytometry (FIG. 3B). In contrast, as shown by the shift to the right of the histograms, representing increased alloantibody binding, challenged mice made increasing levels of both allo-reactive IgG (FIG. 2, panel C) as well as IgM (FIG. 3D). Both classes of allo-reactive antibody increased until week 3 (FIGS. 3C and 3D), after which time the challenge protocol was stopped.

The front histogram in all FIGS. 3A to 3F represents reactivity of serum taken from these mice prior to reconstitution (prebleed), and each successive histogram peak is reactivity of serum taken at the indicated time (weeks post-reconstitution) as indicated on the right y-axis. Sera (1:10 dilution) were incubated with HLA-A2 antigen positive lymphocytes followed by antihuman IgG (FIGS. 3A, 3C and 3E) or antihuman IgM (FIGS. 3B, 3D and 3F) fluorochrome-labelled secondary antibody. A shift of the histogram to the right represents increased alloantibody binding. FIGS. 3A and 3B show findings in a SCID mouse reconstituted but not challenged, FIGS. 3C and 3D in a SCID mouse reconstituted and challenged with HLA-A2 antigen positive lymphocytes, and FIGS. 3E and 3F in a SCID mouse pretreated with anti-asialoGM$_1$ to deplete NK cells, reconstituted and challenged with HLA-A2 antigen positive lymphocytes.

Figure 3E:
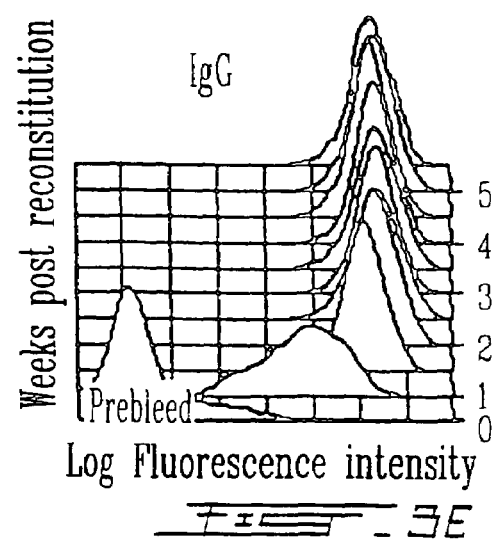
Figure 3F:
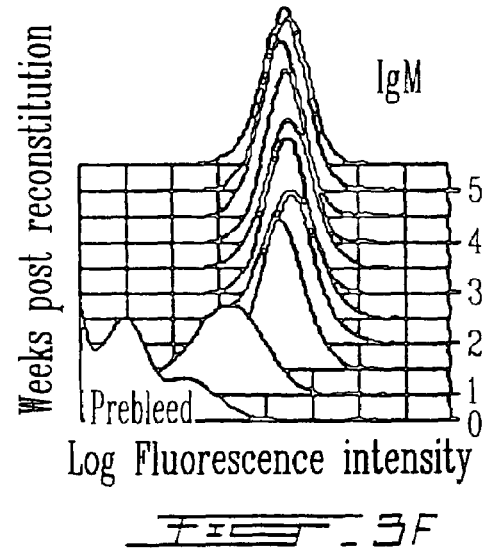

Previous reports have suggested that Nk cells are present in SCID mice. To determine if NK-depleted mice could undergo a better alloantibody response, 14 mice were treated with anti-asialoGM$_1$ (depletes NK cells) one day prior to reconstitution and challenge. NK-depleted challenged mice made significantly more total human IgG and IgM, indicating better overall engraftment (FIGS. 2E and 2F). These NK-depleted challenged mice also produced higher IgG and IgM class alloantibody reactivity (FIGS. 3E and 3F). In addition, these mice attained high steady-state levels of IgG and IgM more rapidly than non-NK-depleted challenged mice (compare FIGS. 3E and 3F to 3C and 3D).

Subsequent evaluation of reducing the numbers of reconstituting PBL of donor "A" in an otherwise identical independent experiment, showed that virtually identical results were obtained with $10^7$ reconstituting cells (i.e. 4 times less reconstituting cells gave rise to a significant and specific alloantibody response to challenge and the magnitude of alloantibody produced was again significantly increased by prior NK cell depletion).

The specificities of the alloantibodies produced in the anti-asialoGM$_1$-treated challenged mice were determined by LCT and the results are shown in Table 1 (columns labelled mouse 1, mouse 2, and mouse 3). The LCT demonstrated complement-fixing alloantibodies to HLA-A2, as well as to the A9, and A28 antigens which share and define the 2C public epitope. Alloantibodies to HLA-B5 were also detected as well as to the B17 and B21 antigens which are known to crossreact strongly with B5. The only other consistent alloantibodies detected were against A10 and B8 which were not detectable in the donors sera nor crossreact with A2 or B5.

To determine the specificity of the IgM alloantibody, the sera from all 3 NK-depleted-challenged mice were pooled and depleted of IgG by two rounds of IgG-specific affinity chromatography. Table 1 shows that the "pooled IgM" class alloantibody reactive with all pertinent HLA-A antigens were observed but B5 was the only HLA-B antigen that reacted with the IgG-depleted sera.

TABLE 1

Summary of anti-HLA specificity by lymphocytotoxicity testing against a 30 cell panel of sera from NK-depleted challenged mice reconstituted with PBL from donor A*

| | pan-HLA challenged | | | | HLA-A2 and B5 challenged | | | |
| --- | --- | --- | --- | --- | --- | --- | --- | --- |
| HLA antigen | Mouse 1 | Mouse 2 | Mouse 3 | Pooled IgM | Mouse 4 | Mouse 5 | Mouse 6 | Mouse 7 |
| A1 | −† | − | − | − | − | − | − | − |
| A2 | + | + | + | + | + | + | + | + |
| A3 | − | − | − | − | − | − | − | − |
| A9 | + | + | + | + | + | + | + | + |
| A10 | + | + | + | w | − | − | − | − |
| A11 | ? | + | ? | − | − | − | − | − |
| A28 | + | + | + | + | + | + | + | + |
| A30 | − | − | − | − | − | − | − | − |
| A31 | − | − | − | − | − | − | − | − |
| A34 | − | − | − | − | − | − | − | − |
| B5 | + | + | + | + | + | + | + | + |
| B7 | − | − | − | − | − | − | − | − |
| B8 | ? | + | + | − | − | − | − | − |

TABLE 1-continued

Summary of anti-HLA specificity by lymphocytotoxicity testing against a 30 cell panel of sera from NK-depleted challenged mice reconstituted with PBL from donor A*

| | pan-HLA challenged | | | | HLA-A2 and B5 challenged | | | |
|---|---|---|---|---|---|---|---|---|
| HLA antigen | Mouse 1 | Mouse 2 | Mouse 3 | Pooled IgM | Mouse 4 | Mouse 5 | Mouse 6 | Mouse 7 |
| B13 | − | − | − | − | − | − | − | − |
| B14 | − | − | − | − | − | − | − | − |
| B16 | − | − | − | − | − | − | − | − |
| B17 | + | + | + | − | | | | |
| B21 | + | + | + | − | | | | |
| B22 | − | ? | − | | | | | |
| B27 | − | − | − | | | − | − | − |
| B37 | − | − | − | | | − | − | − |
| B40 | − | − | − | | | | | |
| B42 | − | − | − | | | | | |
| B44 | − | − | − | | | − | | |
| B75 | − | − | − | − | − | − | − | − |

*The HLA type of donor "A" was HLA-A1, A3, B7, B37: serum from this donor was also assessed by LCT at the time of engraftment and alloantibody reactive with the A2 and B5 antigens only could be detected.
†A negative (−) sign denotes no reactivity with that HLA antigen: a positive (+) sign denotes that sera from that mouse reacted with panel cells expressing the corresponding HLA antigen;
? indicates that reactivity with that HLA antigen could not be verified,
w designates a weak response.

Hu-PBL-SCID mice were repopulated with donor "A" lymphocytes in a separate experiment and were challenged with cells expressing HLA-A2 and B5 as the only HLA antigens foreign to donor "A". These challenged mice made alloantibody against HLA typed panel cells expressing A2, A9, A28, and B5 but not against those expressing A10 or B8 antigens (Table 1, see columns labelled mouse 4 through mouse 7).

Figure 4A:
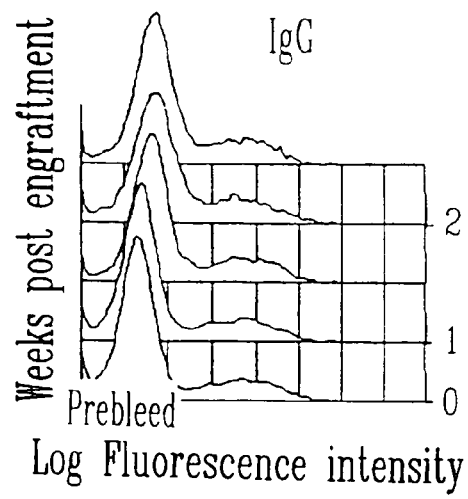
FIGS. 4A to 4F illustrate flow cytometric analysis of alloantibody production in representative SCID mice reconstituted with PBL from a donor previously sensitized to HLA-A10.
Figure 4B:
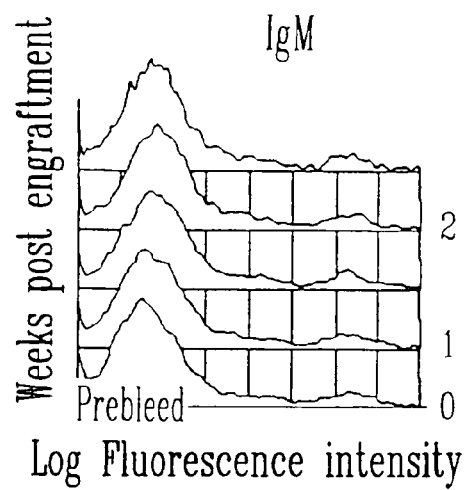
Figure 4C:
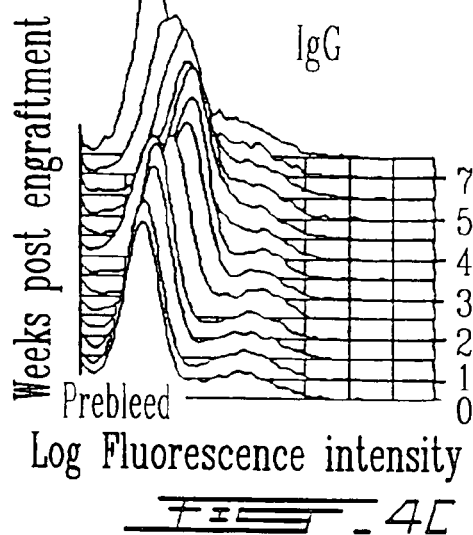
Figure 4D:
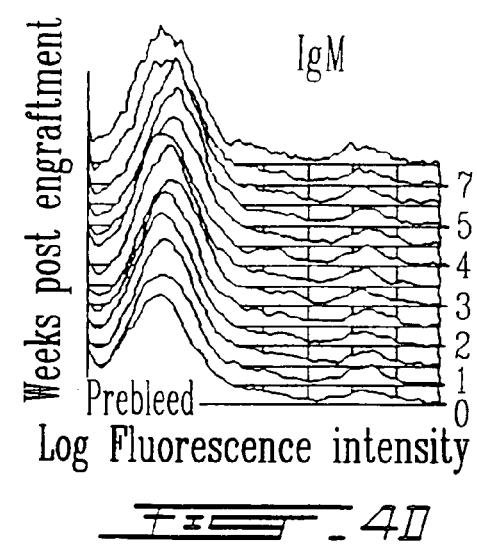
Figure 4E:
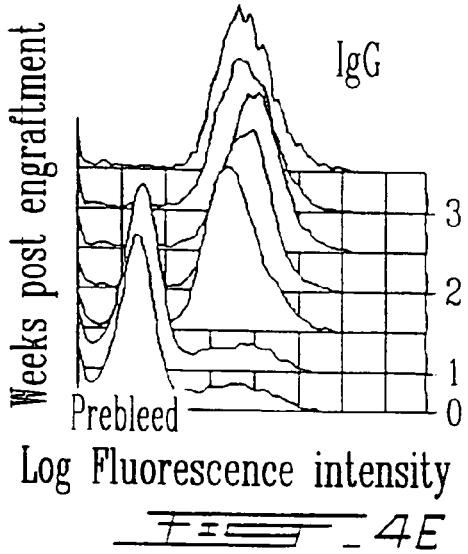

PBL from a blood donor with low levels of serum alloantibody to HLA-A10, B5, B12 and B17 (donor "B") were also used to reconstitute mice. Mice were divided into unchallenged, HLA-A10 challenged, and NK-depleted and HLA-A10 challenged using essentially the same protocol as described for donor "A". Sera (1:10 dilution) from unchallenged, challenged, and NK-depleted challenged Hu-PBL-SCID mice were tested for allo-reactive antibody by flow cytometry against HLA-A10 antigen positive target lymphocytes. Unchallenged donor "B" mice made marginal levels of human IgG and no IgM class alloantibody as assessed by reactivity with HLA-A10 target cells (FIGS. 4A and 4B). However, antigenic challenge of these mice did provoke an allo-response involving IgG but not IgM class antibody (FIGS. 4C and 4D). NK-depleted challenged mice again made a stronger alloantibody response (FIGS. 4E and 4F) than non-NK-depleted challenged mice and this "optimization" of the SCID milieu permitted measurable IgM class alloantibody. As with mice reconstituted with PBL from donor "A", the time to alloantibody detection in donor "B" was more rapid in the NK-depleted challenged mice (compare FIGS. 4C and 4D to FIGS. 4E and 4F). The sera from these mice were subjected to analysis by LCT testing. Alloantibodies were not detected in unchallenged mice but alloantibodies reactive with HLA-A10 were observed in all challenged mice and all anti-asialoGM$_1$-treated-challenged mice.

Figure 4F:
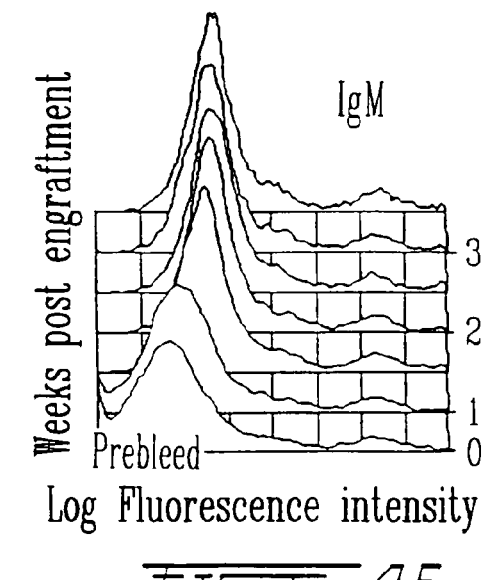

In FIGS. 4A to 4F, sera (1:10 dilution) in this case were incubated with HLA-A10 antigen positive lymphocytes followed by antihuman IgG (FIGS. 4A, 4C and 4E) or anti-human IgM (FIGS. 4B, 4D and 4F). FIGS. 4A and 4B show findings in a SCID mouse reconstituted but not challenged, FIGS. 4C and 4D in a SCID mouse reconstituted and challenged with HLA-A10 antigen positive lymphocytes, and FIGS. 4E and 4F in a SCID mouse pretreated with anti-asialoGM$_1$ to deplete NK cells, reconstituted and challenged with HLA-A10 antigen positive lymphocytes. The mice represented in FIGS. 4A/4B and 4E/4F died after 2½ and 3½ weeks postreconstitution, respectively.

Figure 5:
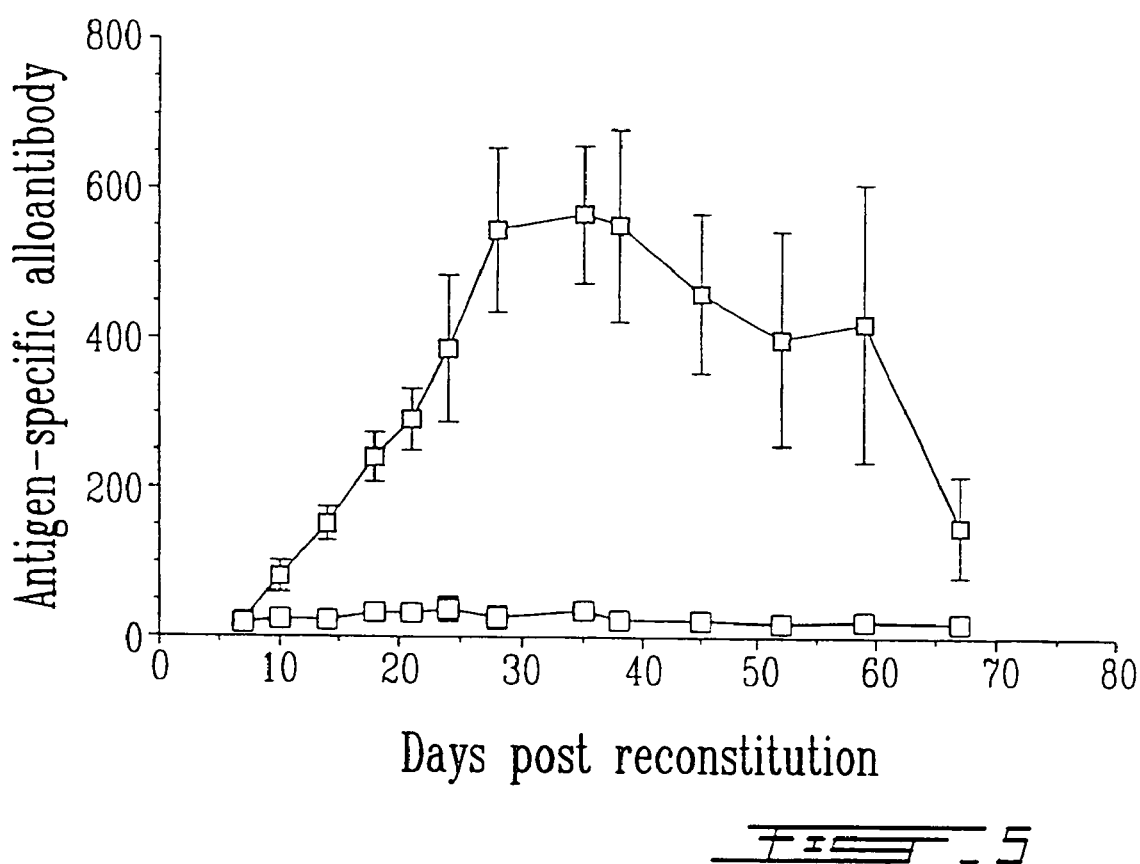
FIG. 5 illustrates a cumulative comparison of alloantibody responses by flow cytometry.

The cumulative flow cytometric data for all donor "A" and "B" reconstituted SCID mice over 5 experiments against antigen positive cells is shown in FIG. 5. The data from the challenged group is the mean reactivity of sera from 22 mice and the unchallenged group is the mean of 13 mice. All NK-depleted challenged mice (22/22) made alloantibody that reacted with antigen positive challenge cells.

Hu-PBL-SCID mice were unchallenged (□, n=13) or challenged with leukocytes (□, n=22) and assessed for IgG class alloantibody reactivity using typed antigen positive cells. The data on the Y-axis is reported as the mean log fluorescence intensity (±SEM) for all mice.

An in vivo model of the secondary immune response was established in a Hu-PBL-SCID mouse model system using lymphocytes from previously sensitized individuals. Intraperitoneal inoculation of SCID mice with these previously sensitized human PBL resulted in engraftment of the mice and challenge with HLA-mismatched lymphocytes resulted in specific alloantibody formation in all mice. This model was used on 12 donors who were not sensitized to HLA antigens. It was found that HLA-specific antibody was never observed. Therefore this model can also be used for defining persons functionally immunized to an antigen as will be described later.

It is known that SCID mice do not contain functional B cells or T cells. The mice do however possess essentially normal NK cells which can inhibit human lymphocyte engraftment and antibody production, likely by destroying the engrafting cells. It has been shown in the present application that pretreatment with anti-asialoGM$_1$ to deplete NK cells resulted in greater IgG and IgM production and in specific alloantibody production over that seen in non-NK-depleted challenged mice. Thus, pretreatment of SCID mice with anti-asialoGM$_1$ did allow maximal alloantibody production.

The lymphocytes used for antigenic challenge of mice reconstituted with PBL from donor "A" were from individuals that were all HLA-A2 antigen positive. Each challenge consisted of lymphocytes derived from between 8–12 different individuals and a different series of individuals was used for each challenge; this was necessary to obtain sufficient PBL for immunization of all mice with the same PBL. Thus, these mice were exposed to lymphocytes from a large number of different donors possessing a wide spectrum of other HLA Class I and Class II antigens in addition to HLA-A2. The response of the mice consisted of alloantibodies to several HLA antigens in addition to A2. The phenomenon of "responders" is well recognized i.e. individuals who make antibody to one challenge are likely to make antibodies to challenge with new immunogenic antigens. These other antibodies could represent primary responses to HLA antigens or secondary responses of previously undetected antibodies, or alloantibodies that are cross reactive with either A2 or B5 which pre-existed in donor "A". The anti-HLA-A alloantibodies produced included anti-A2, -A9, -A10, -A11 and -A28. Since the A9 and A28 antigens are well known to cross react with A2, reactivity with these HLA-A alloantigens is not unexpected. It is however more difficult to account for anti-A10 and A11 reactivity. The anti-A10 and -A11 represent either primary responses, or a secondary response to a putative paternal HLA antigen where the antibody was not initially detectable in the serum of donor "A". Since the paternal HLA typing is unknown, it was not possible to differentiate between these possibilities, however, IgM alloantibody was not produced to the A10 and A11 antigens and therefore the alloantibodies reacting against A10 and A11 are likely an amnestic response. In the case of responses to HLA-B antigens; since donor "A" had pre-existing anti-B5, alloantibody reactive with this antigen is expected. IgM alloantibody reactive with HLA-B antigens could only be detected to B5. Donor A's HLA type was HLA A1, A3, B7 and B37 and none of the mice generated antibodies that reacted with these "self antigens" despite the strong likelihood that the pooled challenge PBL would express these antigens (A1 found in 26% of the Caucasian population, A3 in 25%, and B7 in 22%). This indicates that the mice maintained specificity for foreign antigens without generating auto-reactive antibody. In addition, the fact that challenge with A2- and B5-only expressing cells did not induce formation of A10 and B8 indicates that a generalized immune stimulation was not simply induced but that the allospecificity was maintained for the stimulating cells.

Mice reconstituted with PBL from either donor "A" or "B" made IgM as well as IgG alloantibodies. This is of interest because although IgG is well known to be produced in a secondary response from activation of memory B cell clones, IgM production is not generally considered to be produced by memory B cell clones. Antibodies of the secondary response have however been observed without class switching and experiments with adoptive primary and secondary responses have shown that memory B cells producing IgM can be observed. An alternative explanation may be that these previously sensitized donors possess memory T helper cells to HLA antigens that are able to efficiently activate "naive B cells" to secrete IgM. Coupling of secondary T cell carrier epitopes to primary haptens has been reported to generate primary immunization in Hu-PBL-SCID mice. The T cells most often found in Hu-PBL-SCID mice show the CD45$^{RO}$ memory phenotype and it has been reported that transfer of CD45$^{RO}$, but not CD45$^{RA}$ (naive phenotype), T helper cells could induce purified human B cells in SCID mice to produce immunoglobulin. It is therefore possible that primary IgM-secreting B cells were activated via the memory T cell pool present in the two donors employed for reconstitution of the SCID mice.

Figure 6:
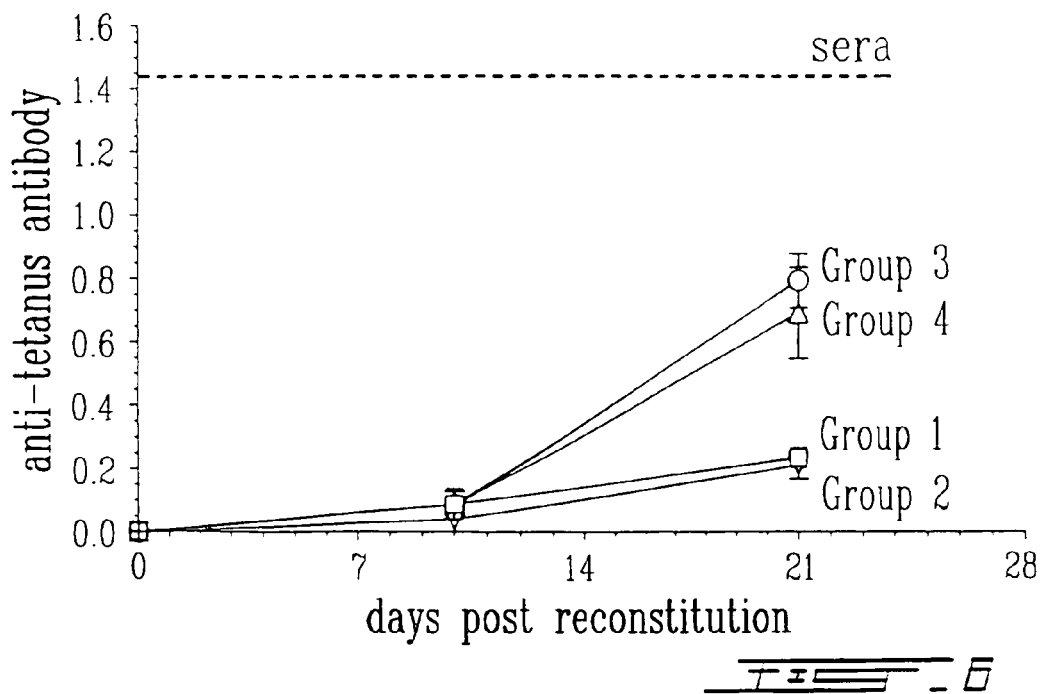
FIG. 6 illustrates Tetanus toxoid specific antibody production in HLA-A2 challenged 18 KDa-CD154 treated Hu-PBL-SCID mice.

To determine if secondary IgG production from memory B cells was a non-specific inhibition by 18 KDa-CD154, the IgG anti-tetanus antibody levels from treated and untreated Hu-PBL-SCID mice were examined. FIG. 6 shows that while stimulation of Hu-PBL-SCID mice with HLA-mismatched lymphocytes caused a slight increase in production of anti-tetanus starting at day 10, the administration of 18 KDa-CD154 did not significantly interfere with the anti-tetanus IgG levels in these four groups of mice (p>0.05). In all cases, the reactivity of an-tetanus IgG in the mice remained well below the levels of anti-tetanus from the donor's serum taken at the time of reconstitution (FIG. 6, dotted line) Hu-PBL-SCID mice as in FIG. 1B were assessed for anti-tetanus toxoid specific antibody. The data on the Y-axis is reported as the mean absorbance (± SEM, n=4 mice per group)

Figure 7:
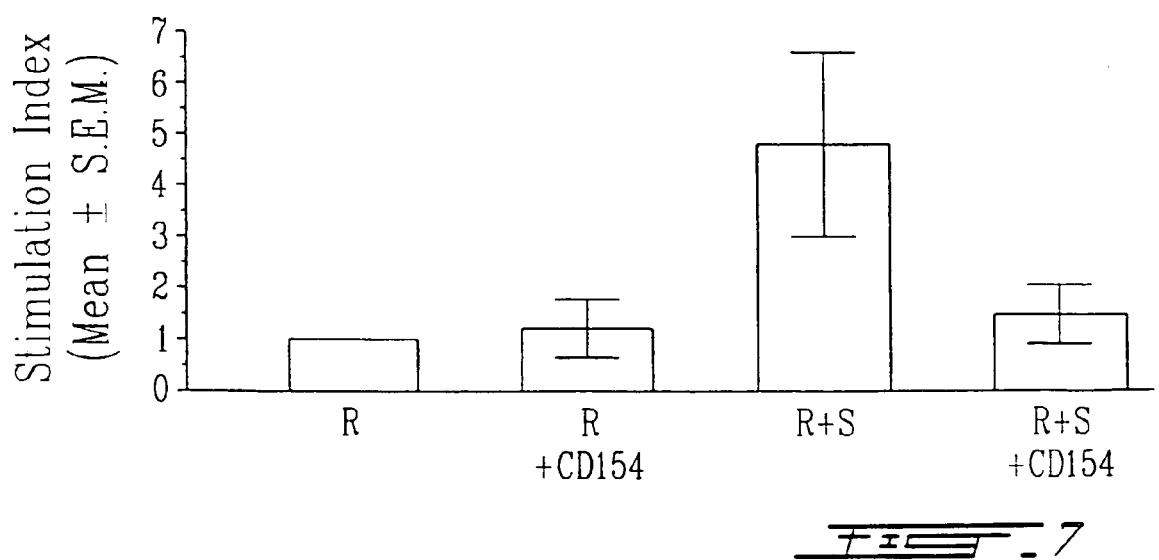
FIG. 7 illustrates mean+SEM stimulation index of a 4 day 1 way mixed lymphocyte culture.

To determine if administration of 18 KDa-CD154 was also able to directly affect cell proliferation, responder cells (from the individual providing the PBL for reconstitution) and stimulator cells (challenge cells) in the presence or absence of 18 KDa-CD154 were set up as mixed lymphocyte cultures. Addition of γ-irradiated stimulator cells to these cultures induced a 4-fold increase in cell proliferation (FIG. 7). Addition of 18 KDa-CD154 to the stimulator+ responder mixed lymphocyte cultures prevented the increase in cell proliferation as compared to the absence of 18 KDa-CD154 (FIG. 7). The stimulation index was calculated by dividing the cpm of cultured responder cells (R) alone by the cpm of responder cells in the presence of A; unstimulated lymphocytes (R), B; lymphocytes reacted with 18 KDa-CD154 (R+CD154) , C: lymphocytes stimulated with γ-irradiated stimulator lymphocytes (R+S), D; lymphocytes stimulated with γ-irradiated stimulator lymphocytes and 18 KDa-CD154 (R+S+CD154)

Accordingly, 18 KDa-CD154 could inhibit alloantibody production by inhibiting T cell activation or T cell function. To test this allegation, mixed lymphocyte cultures were performed and T cell proliferation was shown to be reduced in the presence of 18 KDa-CD154. Since B cells do not play a major role in the mixed lymphocyte culture, T cell activation and proliferation could be directly inhibited by 18 KDa-CD154 treatment. The alloimmune response to blood transfusion has been suggested to be a Th$_2$-dominant immune response. Since CD154 is linked to T cell activation along the Th$_2$ cytokine pathway and T cell proliferation can be defective when IL-4 is absent, the 18 KDa-CD154 fragment have decreased T cell proliferation due to decreased Th$_2$ cytokine production.

It is thus demonstrated in the present application that lymphocytes from individuals previously sensitized to HLA antigens can reconstitute SCID mice and can generate reproducible IgG and IgM allo-immune responses following repeated challenge with selected "foreign" HLA antigens. The development of this model will allow detailed study of the mechanisms of alloimmunization and should facilitate the in vivo assessment of new strategies for the modulation of human alloimmunization to blood cell antigens.

It is also demonstrated in the present application that administration of a recombinant 18 CD154 molecule can inhibit an alloimmune response. This 18 KDa-CD154 molecule may have good therapeutic potential to inhibit human transfusion-induced alloimmunization.

The present invention will be more readily understood by referring to the following examples, which are given to illustrate the invention rather than to limit its scope.

EXAMPLE I

Immunotherapy Drug Screening Design for Alloantibody

SCID mice (or other immunodeficient mice such as NOD-SCID, NUDE, etc . . . ) as prepared in accordance with the present invention are engrafted with human PBL from pregnancy sensitized blood donors and challenged with HLA-mismatched lymphocytes in the presence or absence of any drug or therapeutic (i.e. such as an immunotherapeutic to include IVIG, anti-idiotype antibodies, CTLA4Ig, anti-CD40 ligand antibody, anti-CD40 antibody, anti-CD-4, anti-IL-2 receptor, anti-CD-28, anti-CD-80, anti-CD-86, anti-CD-11A, cyclosporine A, FK506, biologically active peptides such as altered peptide ligands, etc.). The HLA-specific human IgG and IgM were measured as described above.

EXAMPLE II

Evaluation of Functional Immunization of an Individual with an Antigen

Immunodeficient mice such as SCID mice or NOD-SCID mice as prepared in accordance with the present invention are engrafted with PBL from an individual who has been vaccinated (to polio, tetanus, hepatitis B surface antigen, HIV, cancer cells or cancer antigens, etc.) or not. The Hu-PBL-SCID mice are challenged with the same antigen. The antigen-specific human IgG and IgM produced in the mice are measured. The persons exposed to a functional or protective vaccine make antigen-specific or neutralizing IgG and IgM.

EXAMPLE III

Immunotherapy Drug Screening Design for Alloantibody

Immunodificient mice such as SCID mice or NOD-SCID mice as prepared in accordance with the present invention are engrafted with PBL from an individual who has been vaccinated as described in Example II above. The Hu-PBL-SCID mice are challenged with the same antigen in the presence or absence of any drug or therapeutic, such as described in Example I above. The antigen-specific human IgG and IgM are measured as described above.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

The invention claimed is:

1. A method for inhibiting a platelet anti-HLA alloimmune antibody response in a patient comprising the step of administering a therapeutically effective amount of a soluble 18 KDa recombinant human CD40L consisting of amino acids 108 to 261 set forth in SEQ ID NO:1, containing the active binding site of CD40 and capable of binding thereto.

* * * * *